United States Patent [19]
Le Fèvre et al.

[11] Patent Number: 5,998,183
[45] Date of Patent: Dec. 7, 1999

[54] ENZYME IMMOBILIZATION ON A SILICEOUS SUPPORT WITH A POLYALDEHYDE CROSS-LINKING AGENT

[76] Inventors: Gérard N. Le Fèvre, 1409 Harmsworth Square; Bradley A. Saville, 1380 Harmsworth Square, both of Oakville, Canada, L6H 3E7

[21] Appl. No.: 08/888,959

[22] Filed: Jul. 7, 1997

[51] Int. Cl.$^6$ .......................... C12N 11/14; C12N 11/06; C12P 13/06
[52] U.S. Cl. .......................... 435/176; 435/116; 435/181
[58] Field of Search ................................. 435/176, 181, 435/116

[56] References Cited

U.S. PATENT DOCUMENTS

| | | | |
|---|---|---|---|
| 4,071,409 | 1/1978 | Messing et al. | 195/63 |
| 4,072,566 | 2/1978 | Lynn | 195/63 |
| 4,141,857 | 2/1979 | Levy et al. | 252/430 |
| 4,258,133 | 3/1981 | Mirabel et al. | 435/174 |
| 4,384,045 | 5/1983 | Ho et al. | 435/176 |
| 4,888,285 | 12/1989 | Nishimura | 435/176 |
| 5,039,377 | 8/1991 | von Raven et al. | 162/78 |

OTHER PUBLICATIONS

Kinrade, et al., "The Peroxysilicate Question. $^{29}$SI–NMR Evidence for the Role of Silicates in Alkaline Peroxide Brightening of Mechanical Pulp", J. Wood Chem. and Technol., 15(2), 203–222 (1995).

Pialis, et al., "L–DOPA Production from Tyrosinase Immobilized on Nylon 6,6", Biotechnology and Bioengineering, vol. 51, pp. 141–147 (1996).

Murray R. Gray, "Substrate Inactivation of Enzymes In Vitro and In Vivo", Biotech. Adv. vol. 7, pp. 527–575, (1989).

J. Gierer, et al., "Formation of Hydroxyl Radicals from Hydrogen Peroxide and Their Effect on Bleaching of Mechanical Pulps", J. Wood Chem. and Technol. 13(4), 561–581 (1993).

*Primary Examiner*—David M. Naff
*Attorney, Agent, or Firm*—Ridout & Maybee; Randall S. Mitchell

[57] ABSTRACT

A simple, efficient method for immobilization of enzymes on siliceous supports is provided. In a preferred embodiment, a siliceous support having surface hydroxyl groups such as silica gel is contacted with a solution of a polyaldehyde cross-linking agent such as glutaraldehyde to produce a modified support containing bound cross-linking agent. After separation from the solution, the modified support is contacted with a solution containing an enzyme to bind the enzyme to free aldehyde functions of the cross-linking agent. Owing to properties peculiar to siliceous supports, the resulting immobilized enzyme is much more stable than enzymes immobilized on other supports. Consequently, much less enzyme is required. The immobilized enzymes generated via this process are ideally suited for continuous enzymatic production of commodity chemicals and pharmaceuticals such as L-DOPA, and for other enzyme-mediated industrial processes.

9 Claims, No Drawings

ENZYME IMMOBILIZATION ON A SILICEOUS SUPPORT WITH A POLYALDEHYDE CROSS-LINKING AGENT

BACKGROUND OF THE INVENTION

This invention relates to a method for the immobilization of enzymes onto siliceous support materials and the use of such immobilized enzymes in continuous enzyme-based processes such as the production of pharmaceuticals. Immobilized enzymes prepared according to the invention have potential applications, however, in a wide range of synthetic and materials treatment processes such as the production of specialty commodity chemicals, waste water treatment and pulp and paper processing.

The industrial use of enzymes is often limited by their high cost and rapid inactivation. In particular, the use of soluble enzymes necessitates regular replenishment of the enzymes, lost with the product at the conclusion of a process. To improve their economic feasibility in industrial processes, enzymes are generally immobilized onto a matrix. Immobilization facilitates re-use of the enzymes, and may affect the selectivity and stability of the enzyme. Immobilization research has focused upon means to enhance the transfer of enzymes onto the support, and upon means to ensure that the transferred enzymes remain active.

A number of different organic and inorganic support matrices and enzyme immobilization techniques have been tried with a view to achieving a high level of enzyme uptake with a minimum of enzyme degradation or inactivation. One such approach is the immobilization of an enzyme by its physical entrapment within a gel, microcapsule or similar polymeric structure. An example is afforded by U.S. Pat. No. 3,850,751 (Messing) which teaches the adsorption of an enzyme to the inner surface of a porous, essentially non-siliceous ceramic body having an average pore diameter at least as large as the largest dimension of the enzyme.

While entrapment is a simple process and generally affords a high uptake of enzyme without appreciable inactivation during the immobilization process, the enzyme once bound is surrounded by a matrix imposing a mass transfer barrier. In the result, the observed activity may be much lower than the intrinsic activity of the enzyme. On the other hand, direct physical adsorption of the enzyme to a substrate, without any entrapment, is generally characterized by relatively weak binding between enzyme and support, leading to significant enzyme desorption.

Another approach is the direct covalent bonding of an enzyme to a suitably chemically modified support medium. While this leads to strong bonding between the enzyme and the support, a labour-intensive and expensive multi-step procedure is usually involved (including the step of "activating" the support). Too, low enzyme yields are not uncommon, owing to inactivation of the enzyme by the harsh conditions employed in the immobilization process.

A further, widely used approach to enzyme immobilization might be referred to as the "covalent cross-linking" process and is exemplified by U.S. Pat. Nos. 4,071,409 (Messing et al.); 4,258,133 (Mirabel et al.); and 4,888,285 (Nishimura et al.). According to the teachings of these patents a support medium is modified or coated to present functionalities which can then be linked by way of a cross-linking agent to free functional groups on the enzyme. Thus, Nishimura et al. modifies a silica gel or porous glass support surface by reaction with an aminosilane derivative in an organic solvent. The resulting aminated support is then linked to the enzyme in the presence of a polyfunctional cross-linking agent (glutaraldehyde), a phenoxycarboxylic acid (tannic acid) and, optionally, a basic polysaccharide (e.g. chitosan). Nishimura et al. asserts that the tannic acid and chitosan stabilize the enzyme, so as to reduce inactivation by the cross-linking agent during the immobilization process.

According to the aforementioned Mirabel patent, which affords a second example of the covalent cross-linking technique, an inorganic support having surface hydroxyl groups (e.g. brick, alumina, aluminosilicates) is modified with compounds containing an alcohol or phenol group (e.g. monoethanolamine, amino-1 pentanol, p-aminophenol) to generate an ester linkage on a "grafted" support. The resulting grafted support is then coupled to the enzyme, usually in the presence of a bifunctional reagent.

Known enzyme immobilization proceedings employing covalent cross-linking involve in many cases, time consuming modifications to the substrate surface and/or the use of expensive or hazardous reagents (either solvents or the grafting agents themselves).

It is an object of the present invention to provide a simple and efficient method for the immobilization of enzymes on siliceous supports, requiring no prior modification of the support material to avoid the disadvantages attendant on such modification. Our approach is based on the discovery that polyaldehyde cross-linking agents may be used to immobilize enzymes onto previously unmodified siliceous support materials, to produce water-insoluble immobilized enzyme complexes exhibiting high yields of enzyme activity and stability.

It is a further object of the invention to provide immobilized enzymes which may usefully be applied to continuous enzymatic reactions with a variety of industrial applications, including waste water treatment, production of pharmaceuticals and other commodity chemicals, and pulp and paper processing.

SUMMARY OF THE INVENTION

With a view to achieving these objects and overcoming the disadvantage of known enzyme immobilization techniques, there is provided a method for preparing a stable immobilized enzyme having a high yield of enzyme activity, which comprises the steps of (i) incubating a siliceous support material having surface hydroxyl groups with a first aqueous solution containing a polyaldehyde cross-linking agent, under conditions suitable to prepare a support material modified by having at least a portion of the cross-linking agent bound thereto; (ii) removing the modified support material from the solution containing cross-linking agents; (iii) allowing the modified support material to come into contact with an aqueous solution of the enzyme sought to be immobilized, thereby to bind enzyme to free aldehyde functions on the cross-linking agent bound to the support material; and (iv) removing the immobilized enzyme from the enzyme solution, for use in the desired enzymatic reactions.

In a particular useful embodiment of the invention, glutaraldehyde is used to cross-link tyrosinase to an unmodified siliceous support material such as zeolites, sodium aluminosilicate or silica gel, and the immobilized tyrosinase is used in the production of L-DOPA.

GENERAL DESCRIPTION OF THE INVENTION

The present invention is not limited by any particular theory as to the reasons for enhancement of stability of enzymes immobilized on previously unmodified siliceous supports. However, this increased stability is believed to be due to the fact that silicates, including aluminosilicates, are excellent scavengers of superoxide anion, a species believed to be responsible for the inactivation of many enzymes [S. D. Kinrade et al., "The Peroxysilicate Question: $^{29}$SI-NMR Evidence for the Role of Silicates in Alkaline Peroxide Brightening of Mechanical Pulp", J. Wood Chem. Technol. 15(2), 203–222 (1995)]. The protective mechanism is as follows:

Hydroxyl radicals (●OH) can react with the enzyme (E) to yield an inactive oxidized enzyme (Gray, 1989):

$$●OH+E \rightarrow E{-}O+H^+ \qquad (1)$$

Hydroxyl radicals required for reaction (1) can be generated from the reaction of hydrogen peroxide with metals (usually Cu or Fe) within the enzyme (Gray, 1989; J. Gierer et al., "Formation of Hydroxyl Radicals from Hydrogen Peroxide and Their Effect on Bleaching of Mechanical Pulp", J. Wood Chem. Technol. 13, 561 (1993):

$$Cu^+ + H_2O_2 \rightarrow Cu^{2+} + OH^- + ●OH \qquad (2)$$

Hydrogen peroxide may be native to the reaction (as in the production of gluconic acid from glucose mediated by glucose oxidase), or it may be produced indirectly from superoxide anion ($O_2^-●$), via the following two-step process (Gray, 1989):

$$O_2^-● \rightarrow O_2^{2-} + O_2 \qquad (3)$$

$$O_2^{2-} + 2_2O \rightarrow H_2O_2 + 2OH^- \qquad (4)$$

The superoxide anion required for reaction (3) is generated by oxidation of metal, which may be part of the enzyme, or an impurity in the reaction solution:

$$Cu^+ + O_2 \rightarrow Cu^{2+} + O_2^-● \qquad (5)$$

Reaction (5) is inevitable. However, by trapping the superoxide anion generated by reaction (5), the sequence of steps leading to an inactive enzyme (i.e., reaction 3, then 4, then 2, then 1) can be blocked, and enzyme activity can be maintained. The ability of silicates to selectively trap superoxide anion thus leads to dramatically enhanced stability of enzymes when bound to siliceous supports.

The supports covered in this invention include all forms of siliceous materials, including; but not limited to, silica gel, amorphous aluminosilicate, natural or synthetic zeolites (including substituted forms), and natural or synthetic sodium aluminosilicates.

The immobilization method involves the use of a multifunctional cross-linking agent such as glutaraldehyde or other polyaldehydes to couple the enzyme to the support.

Any enzyme may be used in this invention, as long as it is stable during the coupling process between the enzyme and the support. Said enzyme includes, for example, glucose oxidase, polyphenol oxidase, xylanase, catalase, peroxidase, and cellulase.

The immobilized enzyme is prepared via a three-step process. Initially, the support is incubated in an aqueous-based solution containing the cross-linking agent for several hours, at near neutral pH. The concentration of the cross-linking agent is normally up to 3.0% (w/v), but ideally, is approximately 0.5 to 1.5% (w/v). The resulting modified support is then isolated by filtration, and dried.

The second step involves coupling the enzyme to the modified support via the remaining unbound functional groups on the polyfunctional cross-linking agent. In this step, the modified support is incubated in an enzyme-containing aqueous solution (hereafter referred to as the immobilization solution) for several hours at a temperature between 5° C. and 50° C., depending upon the thermal stability of the enzyme. The pH of the immobilization solution is in the range where the enzyme is not inactivated (normally between pH 5 and pH 9). The incubation time is between 1 and 24 hours. For every millilitre of the immobilization solution used, 2 to 5 milligrams of modified support is required.

In the final step, the resulting immobilized enzyme is recovered from the immobilization solution by filtration, then rinsed with water, dried, and stored. This final step removes any loosely bound enzyme from the support. The hydroxyl groups of the support are linked to the amino groups of the protein via the polyfunctional groups of the cross-linking agent, such that the resulting bond between the enzyme and the support is very strong.

According to this invention, as described above, an enzyme can be efficiently and strongly immobilized on a siliceous support. The immobilization procedure provides a high yield of enzyme transferred to the support, and the resulting immobilized enzyme is stable both during storage and during operation. Thus, the immobilized enzyme obtained via this process is well-suited to long-term continuous enzymatic reactions, enhancing productivity while reducing the quantity of enzyme required to achieve a particular degree of conversion.

A detailed description of the invention follows below, with reference to examples for methods for the immobilization of xylanase and tyrosinase onto crystalline sodium aluminosilicate (zeolite A) and onto calcium aluminosilicate.

DETAILED DESCRIPTION OF PREFERRED EMBODIMENTS

EXAMPLE 1

Immobilization of xylanase on crystalline sodium aluminosilicate (zeolite A)

A glutaraldehyde/buffer solution was prepared by mixing sufficient glutaraldehyde in 0.050M phosphate buffer to produce a pH 7 buffer solution containing 1% (w/v) glutaraldehyde.

20 mg of zeolite A was mixed with 50 mL of glutaraldehyde/buffer solution, and incubated at 20° C. for four hours. The mixture was then washed with HPLC grade water, and the remaining (modified) zeolite was recovered by vacuum filtration. The recovered zeolite was dried overnight at room temperature, and weighed.

An enzyme solution was prepared by dissolving 0.0032 g (8000 units) of xylanase in 100 mL of 0.050M citrate buffer (pH 6.5). The resulting immobilization solution had an activity of eight standard units per millilitre of solution.

To immobilize the enzyme, the recovered modified zeolite was incubated in 5 mL of the enzyme solution at 20° C. for 8 hours, under gentle stirring. The mixture was then washed with 0.050M citrate buffer (pH 6.5), and the resulting immobilized enzyme was recovered by vacuum filtration. The recovered enzyme-zeolite powder was left to dry overnight at room temperature.

The fraction of the available xylanase transferred onto the zeolite support was determined by comparing the initial xylanase activity in the immobilization solution with the activity after the immobilization process was complete.

EXAMPLE 2

Immobilization of tyrosinase on crystalline sodium aluminosilicate or calcium aluminosilicate A glutaraldehyde/buffer solution was prepared by mixing sufficient glutaraldehyde in 0.050M phosphate buffer to produce a pH 7 buffer solution containing 1% (w/v) glutaraldehyde.

20 mg of the zeolite support was mixed with 50 mL of glutaraldehyde/buffer solution, and incubated at 20° C. for four hours. The mixture was then washed with HPLC grade water, and the remaining (modified) zeolite was recovered by vacuum filtration. The recovered zeolite was dried overnight at room temperature, and weighed.

An enzyme solution was prepared by dissolving 0.16 mg of tyrosinase (545 Units) in 5.0 mL of 0.050M citrate/HCl buffer solution (pH 6.5). The resulting solution had an activity of 108 standard units per millilitre of solution.

To immobilize the enzyme, the recovered modified zeolite was incubated in 5 mL of the enzyme solution at 20° C. for 24 hours, under gentle stirring. The mixture was then washed with 0.050M citrate buffer (pH 6.5), and the resulting immobilized enzyme was recovered by vacuum filtration. The recovered enzyme-zeolite powder was left to dry overnight at room temperature.

The fraction of the available tyrosinase transferred onto the zeolite support was determined by comparing the initial tyrosinase activity in the immobilization solution with the activity after the immobilization process was complete.

COMPARATIVE EXAMPLE 2

Immobilization of tyrosinase on nylon 6,6

Membranes of nylon 6,6 were modified by soaking in water for 24 h, then in 3.0M HCl for 10 minutes, and again in water. The membrane was then incubated for 24 h in a 50 mL solution of N,N'dicyclohexylcarbodiimide (1% w/v) and 3,3',5,5'-tetramethylbenzidine (1% w/v) in methylene chloride. The membrane was then washed with, in order, methylene chloride, acetone, and water. The modified nylon membrane was then immersed in a 50 mL solution of glutaraldehyde (3% w/v) in 0.10M phosphate buffer (pH 8), and soaked for 2.5 h at 4° C., with gentle stirring. The membrane was the washed with phosphate buffer, and incubated for 24 h at 20° C. in a 30 mL solution of 0.10M phosphate buffer (pH 7) containing 12,300 units of tyrosinase. The membrane with the immobilized tyrosinase was washed in phosphate buffer, then stored in a saline solution (9 g/L) at 4° C. until needed for use.

The fraction of the available tyrosinase transferred onto the modified nylon support was determined by comparing the initial tyrosinase activity in the immobilization solution with the activity after the immobilization process was complete.

EXAMPLE 3

L-DOPA production using tyrosinase immobilized on crystalline sodium aluminosilicate (zeolite A)

The immobilized enzyme was circulated throughout a batch reactor containing 2.5 mM L-tyrosine and 2.5 mM L-ascorbate in phosphate buffer (pH 6.5) at 22° C. The rate of L-DOPA production was monitored over 7 hours.

COMPARATIVE EXAMPLE 3

L-DOPA production using tyrosinase immobilized on nylon 6,6

The nylon membrane (containing the enzyme) was immersed in a batch reactor containing 2.5 mM L-tyrosine and 2.5 mM L-ascorbate in phosphate buffer (pH 6.5) at 22° C. The rate of L-DOPA production was monitored over 7 hours.

EXAMPLE 4

Stability of tyrosinase immobilized on crystalline sodium aluminosilicate and calcium aluminosilicate (zeolites)

The stability of the enzyme under standard operating conditions was determined by comparing the activity of the enzyme at various stages during repeated-batch production of L-DOPA from L-tyrosine. The half life is defined as the time required for the initial activity to be reduced by 50%.

RESULTS (A) Up to 40% of the available xylanase was transferred to the zeolite support. Studies with the immobilized enzyme demonstrated that the enzyme was active and stable.

(B) In Table 1, the fraction of available tyrosinase transferred to zeolite supports is compared with the immobilization yield observed using other supports and immobilization methods.

TABLE 1

Immobilization Yield of Tyrosinase on Various Supports

| Support; Enzyme Units Required[1] | Immobilization Method | Immobilization Yield |
|---|---|---|
| Nylon 6 gels; chemically modified with benzidine, isonitrile, dimethylpropanediamine, or diaminodiphenylmethane (88,400 units) | Covalent cross-linking to chemically modified nylon gels using either glutaraldehyde, acetaldehyde, or nitrite | 33–76% |
| Collagen membranes; chemically modified with dimethyladipimidate or ethyl acetimidate (1496000 units) | covalent cross-linking to chemically modified membranes using glutaraldehyde | 75% |
| Enzacryl AA*; activated by diazotation with nitric acid (5 units of proenzyme, subsequently activated) | covalent cross-linking to arylamine groups on the support via tyrosine residues | 79% |
| Magnetite; activated with 3 aminopropyltriethoxysilane (3400 units) | covalent cross-linking using glutaraldehyde | 70–80% |
| Nylon 6,6 membranes; chemically modified with benzidine and carbodiimide (12320 units) | covalent cross-linking to modified support using glutaraldehyde | 63–73% |
| Zeolites (545 units) | covalent cross-linking to unmodified support using polyaldehydes | 82–89% |

[1]Enzyme Units Required (in parentheses) indicates the quantity of enzyme in the solution at the beginning of the immobilization process.
*trademark for polyacrylic support material The rate of L-DOPA production using tyrosinase immobilized on a variety of supports is illustrated in Table 2. Clearly, the tyrosinase immobilized on zeolites provides superior productivity, while reducing the enzyme requirement dramatically.

TABLE 2

Production of L-DOPA Using Tyrosinase Immob. on Various Supports

| Support | Enzyme Requirement, Units[1] | Average Production Rate, mg $L^{-1}$ $h^{-1}$ | Duration | Maximum Production Rate, mg $L^{-1}$ $h^{-1}$ |
|---|---|---|---|---|
| Nylon 6,6 membranes | 12,300 | 33 | 7h | 88 |
| Enzacryl AA | 5[2] | 27.6 | 8h | 70 |
| Zeolite A | 545 | 34 | 7h | 92 |
| Zeolite A, repeated batch | 545 | 54 | 40 | 215 |

[1]Enzyme Requirement refers to the amount of enzyme required for immobilization; the immobilized enzyme, when used to produce L-DOPA, leads to the specified production rates. Unless specified, Mushroom tyrosinase was used.
[2]Proenzyme from frog epidermis, which is subsequently activated using trypsin and sepharose.

C) L-DOPA Stability

As shown in Table 3, the observed stability of tyrosinase immobilized on zeolites is much superior to the stability of tyrosinase immobilized on other supports, when used for the same biochemical transformation.

TABLE 3

Half Life of Tyrosinase on Various Supports

| Support | Half Life |
|---|---|
| Nylon 6 gels | 3.5–11h |
| Collagen membranes | 1.5h |
| Enzacryl AA | 6.5h |
| Nylon 6,6 membranes | 46h |
| Zeolites | No loss of activity over 40h |

We claim:

1. A method for preparing a stable immobilized enzyme having a high yield of enzyme activity, comprising the steps of:

(a) incubating a siliceous support material having surface hydroxyl groups with a first aqueous solution containing a polyaldehyde cross-linking agent, under conditions suitable to prepare a modified support material having at least a portion of said cross-linking agent bonded thereto without prior exposure of said siliceous support material to any reagent for coupling said polyaldehyde cross-linking agent to the surface of the support material;

(b) removing said modified support material from said first aqueous solution;

(c) allowing a second aqueous solution containing an enzyme to come into contact and remain in contact with said modified support material to bind enzyme to free aldehyde functions on said bound cross-linking agent; and (d) removing the support material with bound immobilized enzyme from said second aqueous solution.

2. A method according to claim 1, wherein said polyaldehyde cross-linking agent is glutaraldehyde.

3. A method according to claim 2, wherein said siliceous support material is selected from the group consisting of natural or synthetic zeolites, natural or synthetic sodium aluminosilicate, amorphous aluminosilicate and silica gel.

4. A method according to claim 3, wherein said enzyme is xylanase.

5. A method according to claim 3, wherein said enzyme is tyrosinase.

6. An immobilized enzyme, produced by the method comprising the steps of:

(a) incubating a siliceous support material having surface hydroxyl groups with a first aqueous solution containing a polyaldehyde cross-linking agent, under conditions suitable to prepare a modified support material having at least a portion of said cross-linking agent bonded thereto without prior exposure of said siliceous support material to any reagent for coupling said polyaldehyde cross-linking agent to the surface of the support material;

(b) removing said modified support material from said first aqueous solution:

(c) allowing a second aqueous solution containing an enzyme to come into contact and remain in contact with said modified support material to bind enzyme to free aldehyde functions on said bound cross-linking agent, thereby immobilizing the enzyme; and (d) recovering the resultant immobilized enzyme from said second aqueous solution.

7. An immobilized enzyme according to claim 6, wherein said siliceous support material is selected from the group consisting of natural or synthetic zeolites, natural or synthetic sodium aluminosilicate, amorphous aluminosilicate and silica gel.

8. An immobilized enzyme according to claim 7, wherein said polyaldehyde cross-linking agent is glutaraldehyde.

9. An immobilized enzyme according to claim 8, wherein said enzyme is tyrosinase.

* * * * *